US008017729B2

(12) United States Patent
Shiba et al.

(10) Patent No.: US 8,017,729 B2
(45) Date of Patent: Sep. 13, 2011

(54) NANOGRAPHITE STRUCTURE/METAL NANOPARTICLE COMPOSITE

(75) Inventors: Kiyotaka Shiba, Kawasaki (JP); Kenichi Sano, Tokyo (JP); Kenji Iwahori, Nara (JP)

(73) Assignee: Japan Science and Technology Agency, Saitama (JP)

( * ) Notice: Subject to any disclaimer, the term of this patent is extended or adjusted under 35 U.S.C. 154(b) by 1001 days.

(21) Appl. No.: 11/767,583

(22) Filed: Jun. 25, 2007

(65) Prior Publication Data

US 2010/0029910 A1 Feb. 4, 2010

Related U.S. Application Data

(63) Continuation-in-part of application No. PCT/JP2005/023675, filed on Dec. 22, 2005.

(30) Foreign Application Priority Data

Dec. 24, 2004 (JP) ................................ 2004-374093

(51) Int. Cl.

| | |
|---|---|
| ***A61K 38/00*** | (2006.01) |
| ***A61K 38/04*** | (2006.01) |
| ***C07K 5/00*** | (2006.01) |
| ***C07K 7/00*** | (2006.01) |
| ***C07K 16/00*** | (2006.01) |
| ***C07K 17/00*** | (2006.01) |

(52) U.S. Cl. ........ 530/328; 530/326; 530/327; 530/329; 530/330

(58) Field of Classification Search ........................ None
See application file for complete search history.

(56) References Cited

U.S. PATENT DOCUMENTS 7,462,462 B2 * 12/2008 Shiba et al. .................... 435/7.5
2003/0113714 A1 * 6/2003 Belcher et al. .................... 435/5

FOREIGN PATENT DOCUMENTS

JP 2001-181842 7/2001
JP 2004-121154 4/2004

OTHER PUBLICATIONS

Allen et al. Protein Cage Constrained Synthesis of Ferrimagnetic Iron Oxide Nanoparticles. Advanced Materials. 2002, vol. 14, No. 21, pp. 1562-1565.*

Diameter-Controlled Growth of Multi-Walled Carbon Nanotubes by Hot-Filament Chemical Vapor Deposition with Ferritin as a Catalyst on a Silicon Substrate. Japanese Jornal of Applied Physics. 2005. vol. 44, Nol. 7A, pp. 5292-5295.*
H.J.C. Berendsen. A Glimpse of the Holy Grail? Science (1998) 282, pp. 642-643.*
Rudinger. In: Peptide Hormones, JA Parsons, Ed. (1976) pp. 1-7.*
Sigma. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://ww.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Journal of Biological Chemistry, 1983, 258: 10873-10880.
Journal of Nuclear Medicine, 1983, 24: 608-614.
Journal of Biological Chemistry, 1986, 261: 6677-6683.
Proceedings of the National Academy of Sciences, 1992, 89: 11064-11068.
Bulletin of Environmental Contamination and Toxicology, 1970, 5: 115-124.
Bulletin of the Chemical Society of Japan, 2005, 78: 2075-2081.
Biotechnology and Bioengineering, 2003, 84: 187-194.
Chemistry Letters, 2004, 33: 1158.
Inorganic Chemistry, 2005, 44: 6393-6400.
46th Annual Meeting of the Biophysical Society of Japan, IP-307.
Chemistry of Materials, 2007, 19: 3105-3111.

* cited by examiner

*Primary Examiner* — Marcela M Cordero Garcia
(74) *Attorney, Agent, or Firm* — Frommer Lawrence & Haug LLP

(57) ABSTRACT

The present invention makes it possible to efficiently recognize carbon nanotubes, carbon nanohorns or modifiers thereof and to support functional compounds by fusing the ability of ferritin molecules capable of forming nanoparticles of inorganic metal atoms or inorganic metal compounds. In addition, because ferritin molecules are capable of forming two-dimensional crystals at the interface, the present invention makes it possible to align carbon nanotubes, carbon nanohorns with the use of the molecular arrangement ability of ferritin fused with nanographite structure recognition peptides. A nanographite structure/metal nanoparticle composite is constructed, wherein a nanoparticle of an inorganic metal atom or an inorganic metal compound is retained in an interior space of a protein in which a nanographite structure recognition peptide is fused or chemically bound to a surface of a cage protein such as ferritin, and wherein a plurality of nanoparticles of an inorganic metal atom or an inorganic metal compound are supported on a nanographite structure with the use of affinity of the nanographite structure recognition peptide to the nanographite structure.

15 Claims, 5 Drawing Sheets control LFO N1-LF

SEQUENCE LISTING

```
<160> NUMBER OF SEQ ID NOS: 26

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:pNHD12-5-2

<400> SEQUENCE: 1

Asp Tyr Phe Ser Ser Pro Tyr Tyr Glu Gln Leu Phe
```

1 5 10

<210> SEQ ID NO 2
<211> LENGTH: 7
<212> TYPE: PRT
<213> ORGANISM: Artificial Sequence
<220> FEATURE:
<223> OTHER INFORMATION: domain recognizing nanographite structure

<400> SEQUENCE: 2

Tyr Asp Pro Phe His Ile Ile
1 5

<210> SEQ ID NO 3
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 3

Gly His Trp His His Ile Thr Lys Val Ser Lys Gln
1 5 10

<210> SEQ ID NO 4
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 4

Trp Pro Gly Trp His His Val Pro Pro Ala Val Ser
1 5 10

<210> SEQ ID NO 5
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 5

Ser Trp His His Lys His Gly Val Asp Tyr Arg Pro
1 5 10

<210> SEQ ID NO 6
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 6

Trp His Pro Gln Gln His Trp Phe Asp His Ser His
1 5 10

<210> SEQ ID NO 7
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 7

Ser Ser Pro Tyr Trp Ser Lys Pro Pro Val Arg Trp
1 5 10

<210> SEQ ID NO 8
<211> LENGTH: 7
<212> TYPE: PRT
<213> ORGANISM: Artificial Sequence
<220> FEATURE:
<223> OTHER INFORMATION: domain recognizing nanographite structure

<400> SEQUENCE: 8

Tyr Tyr Pro His Pro Met Phe
1 5

<210> SEQ ID NO 9
<211> LENGTH: 7
<212> TYPE: PRT
<213> ORGANISM: Artificial Sequence
<220> FEATURE:
<223> OTHER INFORMATION: domain recognizing nanographite structure

<400> SEQUENCE: 9

Asn Trp Trp Asn His Ala Arg
1 5

<210> SEQ ID NO 10
<211> LENGTH: 7
<212> TYPE: PRT
<213> ORGANISM: Artificial Sequence
<220> FEATURE:
<223> OTHER INFORMATION: domain recognizing nanographite structure

<400> SEQUENCE: 10

Thr Trp Gly His Gln Phe Gly
1 5

<210> SEQ ID NO 11
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 11

Thr Trp Trp Pro Tyr Ala His Ser Thr Thr Pro Arg
1 5 10

<210> SEQ ID NO 12
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 12

Gly Trp Trp Ser Arg Pro Met Asn His Ile Tyr Ala
1 5 10

<210> SEQ ID NO 13
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 13

Tyr Phe Ser Trp Tyr Gly Arg His Tyr Ala Asn Pro
1 5 10

<210> SEQ ID NO 14

<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 14

His Tyr Ser Trp Trp Arg Ala Pro Thr Pro Thr Pro
1 5 10

<210> SEQ ID NO 15
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 15

Thr Trp Trp Gly Pro His Ala Val Gln Met His Thr
1 5 10

<210> SEQ ID NO 16
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 16

Ser His Trp Trp Ser Trp Thr Thr Pro Leu Asn Gly
1 5 10

<210> SEQ ID NO 17
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 17

Ser Trp Trp Asn Trp Arg Leu Pro Ser Pro Pro Gln
1 5 10

<210> SEQ ID NO 18
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 18

Ser Asn Trp Trp Pro His Pro Thr Ser Leu Arg Trp
1 5 10

<210> SEQ ID NO 19
<211> LENGTH: 12
<212> TYPE: PRT
<213> ORGANISM: Artificial Sequence
<220> FEATURE:
<223> OTHER INFORMATION: domain recognizing nanographite structure

<400> SEQUENCE: 19

Thr Trp Trp Gly Pro Trp Trp Ser Lys Thr Ala Ile
1 5 10

<210> SEQ ID NO 20
<211> LENGTH: 12
<212> TYPE: PRT

<213> ORGANISM: Artificial Sequence
<220> FEATURE:
<223> OTHER INFORMATION: domain recognizing nanographite structure

<400> SEQUENCE: 20

```
Ser His Trp Trp Trp Trp Asp Ala Arg Gly Tyr Asp
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: peptide

<400> SEQUENCE: 21

```
Asp Tyr Pro Ser Ser Pro Tyr Tyr Glu Gln Leu Phe
1               5                   10
```

<210> SEQ ID NO 22
<211> LENGTH: 48
<212> TYPE: DNA
<213> ORGANISM: Artificial Sequence
<220> FEATURE:
<223> OTHER INFORMATION: sense primer

<400> SEQUENCE: 22

```
gatccatgga ttatttctcg agcccgtatt atgaacagct gtttagct                  48
```

<210> SEQ ID NO 23
<211> LENGTH: 40
<212> TYPE: DNA
<213> ORGANISM: Artificial Sequence
<220> FEATURE:
<223> OTHER INFORMATION: antisense primer

<400> SEQUENCE: 23

```
aaacagctgt tcataatacg ggctcgagaa ataatccatg                           40
```

<210> SEQ ID NO 24
<211> LENGTH: 15
<212> TYPE: DNA
<213> ORGANISM: Artificial Sequence
<220> FEATURE:
<223> OTHER INFORMATION: sequence primer DNA

<400> SEQUENCE: 24

```
gtggaattgt gagcg                                                      15
```

<210> SEQ ID NO 25
<211> LENGTH: 175
<212> TYPE: PRT
<213> ORGANISM: Artificial Sequence
<220> FEATURE:
<223> OTHER INFORMATION: LF0

<400> SEQUENCE: 25

```
Met Ser Ser Gln Ile Arg Gln Asn Tyr Ser Thr Glu Val Glu Ala Ala
1               5                   10                  15

Val Asn Arg Leu Val Asn Leu Tyr Leu Arg Arg Ser Tyr Thr Tyr Leu
            20                  25                  30

Ser Leu Gly Phe Tyr Phe Asp Arg Asp Asp Val Ala Leu Glu Gly Val
        35                  40                  45

Cys His Phe Phe Arg Glu Leu Ala Glu Glu Lys Arg Glu Gly Ala Glu
    50                  55                  60
```

Arg Leu Leu Lys Met Gln Asn Gln Ala Gly Gly Arg Ala Leu Phe Gln
65 70 75 80

Asp Leu Gln Lys Pro Ser Gln Asp Glu Trp Gly Thr Thr Pro Asp Ala
85 90 95

Met Lys Ala Ala Ile Val Leu Glu Leu Ala Leu Asn Gln Ala Leu Leu
100 105 110

Asp Leu His Ala Leu Gly Ser Ala Gln Ala Asp Pro His Leu Cys Asp
115 120 125

Phe Leu Glu Ser His Phe Leu Asp Glu Glu Val Lys Leu Ile Lys Lys
130 135 140

Met Gly Asp His Leu Thr Asn Ile Gln Arg Leu Val Gly Ser Gln Ala
145 150 155 160

Gly Leu Gly Glu Trp Leu Phe Glu Arg Leu Thr Leu Lys His Asp
165 170 175

<210> SEQ ID NO 26
<211> LENGTH: 187
<212> TYPE: PRT
<213> ORGANISM: Artificial Sequence
<220> FEATURE:
<223> OTHER INFORMATION: N1-LF

<400> SEQUENCE: 26

Met Asp Tyr Phe Ser Ser Pro Tyr Tyr Glu Gln Leu Phe Ser Ser Gln
1 5 10 15

Ile Arg Gln Asn Tyr Ser Thr Glu Val Glu Ala Ala Val Asn Arg Leu
20 25 30

Val Asn Leu Tyr Leu Arg Ala Ser Tyr Thr Tyr Leu Ser Leu Gly Phe
35 40 45

Tyr Phe Asp Arg Asp Asp Val Ala Leu Glu Gly Val Cys His Phe Phe
50 55 60

Arg Glu Leu Ala Glu Glu Lys Arg Glu Gly Ala Glu Arg Leu Leu Lys
65 70 75 80

Met Gln Asn Gln Arg Gly Gly Arg Ala Leu Phe Gln Asp Leu Asp Lys
85 90 95

Pro Ser Gln Asp Glu Trp Gly Thr Thr Pro Asp Ala Met Lys Ala Ala
100 105 110

Ile Val Leu Glu Lys Ser Leu Asn Gln Ala Leu Leu Asp Leu His Ala
115 120 125

Leu Gly Ser Ala Gln Ala Asp Pro His Leu Cys Asp Phe Leu Glu Ser
130 135 140

His Phe Leu Asp Glu Glu Val Lys Leu Ile Lys Lys Met Gly Asp His
145 150 155 160

Leu Thr Asn Ile Gln Arg Leu Val Gly Ser Gln Ala Gly Leu Gly Glu
165 170 175

Tyr Leu Phe Glu Arg Leu Thr Leu Lys His Asp
180 185

NANOGRAPHITE STRUCTURE/METAL NANOPARTICLE COMPOSITE

INCORPORATION BY REFERENCE

This application is a continuation-in-part application of international patent application Serial No. PCT/JP2005/023675 filed Dec. 22, 2005 and published as WO 2006/068250 on Jun. 29, 2006, which claims priority to Japanese patent application Serial No. JP 2004-374093 filed Dec. 24, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a protein wherein a nanographite structure recognition peptide is fused or chemically bound to the surface of a cage protein such as ferritin, and a nanographite structure/metal nanoparticle composite constructed with the use of the protein, wherein a plurality of nanoparticles of an inorganic metal atom or an inorganic metal compound are supported on the nanographite structure, etc. For example, a nanographite structure/metal nanoparticle composite, wherein a plurality of nanoparticles are supported through a compound of graphite structure having a nanometer-scale fine structure and a cage protein such as fusion ferritin which recognizes the compound specifically, can be advantageously used for semiconductors, nanobiotechnology, etc.

BACKGROUND OF THE INVENTION

Diamond and graphite, as crystal structures of carbon, have been well known in the field. C60 was found in 1985 by R. E. Smalley, R. F. Curl and H. W. Kroto et al. (for example, Nature, 318: 162-163, 1985), and has a soccer ball-like structure comprising 12 pentagons and 20 hexagons. In addition to C60, there are other large basket-like molecules such as C70 and C76. This series of molecules is called "fullerene." Carbon compounds with structures that were previously unknown, such as "carbon nanotube" (Nature, 354: 56-58, 1991; Japanese Laid-Open Patent Application No. 2001-64004) and "carbon nanohorn" (Chem. Phys. Lett., 309: 165-170, 1999; Japanese Laid-Open Patent Application No. 2001-64004), were successively discovered by Sumio Iijima, in 1991 and 1999, respectively. All of these fullerenes, carbon nanotubes and carbon nanohorns comprise six- and five-membered rings of carbon atoms, and form nanometer-scale fine structures; therefore, they have recently attracted a lot of attention as "nanographite structures".

There are many reasons that nanographite structures are of particular interest in the field. For example, "carbon nanotubes can have both properties of metal and semiconductor due to the difference in their chirality" (Nature, 391: 59-62), and "metal-doped fullerene exhibits superconductivity" (Nature, 350: 600-601). Furthermore, nanographite structures attract attention because of the "selective gas storage capability shown by carbon nanohorns" (Nikkei Science, 42, August issue, 2002), the "ability of carbon nanohorn for the support and sustained release of pharmaceutical compounds" (Japanese Patent Application No. 2004-139247; Mol Pharmaceutics 1: 399), and the like. With the use of these characteristic properties, nanographite structures may be applied to new electrical materials, catalysts, optical materials, and other fields; in particular, they may be used for wiring of semiconductors, fluorescent indicator tubes, fuel cells, gas storage, vectors for gene therapy, cosmetics, drug delivery systems, biosensors, etc.

The present inventors and others have isolated a peptide motif which binds to a carbon nanohorn, one of nanographite structures, by the phage display technique (Japanese Laid-Open Patent Application No. 2004-121154; Langmuir, 20, 8939-8941, 2004).

On the other hand, ferritin proteins have been well known as a protein which stores "molecules of 'iron,' which is an essential metal and is toxic at the same time" in living bodies. Ferritin exists universally, from animals and plants to bacteria, and is deeply involved in the homeostasis of iron element in living bodies or in cells. Ferritin from higher eukaryotes such as human and horse forms a spherical shell structure consisting of a 24-mer approximately 12 nm in diameter, formed from peptide chains whose molecular weight is about 20 kDa, and has an interior space of 7 to 8 nm. Ferritin stores iron molecules in this interior space as a mass of nanoparticulate iron oxide. With regard to 24 subunits which constitute a protein spherical shell (cage), there are two types (type H and type L), and the ratio of these types varies depending on organism species and tissues.

Ferritin stores iron nanoparticles inside it under natural circumstances. However, under artificial circumstances, it has been revealed that ferritin can store the substances in addition to iron such as oxides of beryllium, gallium, manganese, phosphorus, uranium, lead, cobalt, nickel, chromium, etc., and nanoparticles of semiconductors, magnets such as cadmium selenide, zinc sulfide, iron sulfide and cadmium sulfide. Consequently, applied research of ferritin in the fields of material engineering of semiconductors and health care has been actively conducted.

If it is possible to combine nanographite structures having excellent properties with metal-filled ferritin molecules, the development of composite materials having an unprecedented new function can be expected. In this case, a technique for making ferritin molecules efficiently recognize and bind to nanographite structures such as carbon nanotubes and carbon nanohorns, is required.

Citation or identification of any document in this application is not an admission that such document is available as prior art to the present invention.

SUMMARY OF THE INVENTION

An objective of the present invention is to make it possible to efficiently recognize carbon nanotubes, carbon nanohorns or modifiers thereof and to support functional compounds thereon by fusing ferritin molecules capable of forming nanoparticles of inorganic metal atoms or inorganic metal compounds with nanographite structure recognition peptides. In addition, because ferritin molecules are capable of forming two-dimensional crystals at the interface and have ability for molecular arrangement, an objective of the present invention is to make it possible to align carbon nanotubes, carbon nanohorns with the use of the molecular arrangement ability of ferritin fused with nanographite structure recognition peptides.

The present inventors have made a keen study for solving the above-mentioned objectives and have confirmed that a plurality of nanoparticles may be supported on a nanographite structure by the process comprising the following steps: (1) fusing cDNA encoding the amino-terminal of horse spleen-derived type L ferritin molecule with DNA encoding a peptide consisting of the amino acid sequence shown by SEQ ID NO: 1; (2) expressing a protein having the amino acid sequence shown by SEQ ID NO: 26 with the use of *E. coli*; (3) purifying the protein; and (4) retaining nanoparticles of metal oxide in the interior space of the fusion protein thus obtained. This led to the completion of the present invention.

In other words, the present invention relates to: (1) a nanographite structure/metal nanoparticle composite, wherein a nanoparticle of an inorganic metal atom or an inorganic metal compound may be retained in an interior space of a protein in which a nanographite structure recognition peptide may be fused or chemically bound to a surface of a cage protein, and wherein a plurality of nanoparticles of an inorganic metal atom or an inorganic metal compound may be supported on a nanographite structure with the use of affinity of the nanographite structure recognition peptide to the nanographite structure; (2) the nanographite structure/metal nanoparticle composite according to (1) mentioned above, wherein the cage protein may belong to a ferritin protein family; (3) the nanographite structure/metal nanoparticle composite according to (2) mentioned above, wherein the ferritin protein family may be ferritin; (4) the nanographite structure/metal nanoparticle composite according to (3) mentioned above, wherein the ferritin may be higher eukaryote-derived ferritin; (5) the nanographite structure/metal nanoparticle composite according to (4) mentioned above, wherein the higher eukaryote-derived ferritin may be horse spleen-derived type L ferritin; (6) the nanographite structure/metal nanoparticle composite according to (1) mentioned above, wherein the cage protein may be derived from a bacterium; (7) the nanographite structure/metal nanoparticle composite according to (1) mentioned above, wherein the cage protein may be a viral particle; (8) the nanographite structure/metal nanoparticle composite according to any one of (1) to (7) mentioned above, wherein the nanographite structure recognition peptide may be a peptide consisting of an amino acid sequence shown by any one of SEQ ID NOs: 1 to 20; (9) the nanographite structure/metal nanoparticle composite according to any one of (1) to (7) mentioned above, wherein the nanographite structure recognition peptide may be a peptide containing whole or part of an amino acid sequence shown by any one of SEQ ID NOs: 1 to 20 and may be capable of binding to a nanographite structure; (10) the nanographite structure/metal nanoparticle composite according to (8) or (9) mentioned above, wherein the amino acid sequence shown by any one of SEQ ID NOs: 1 to 20 may be DYFSSPYYEQLF (SEQ ID NO: 1); (11) the nanographite structure/metal nanoparticle composite according to (8) or (9) mentioned above, wherein the amino acid sequence shown by any one of SEQ ID NOs: 1 to 20 may be YDPFHII (SEQ ID NO: 2); (12) the nanographite structure/metal nanoparticle composite according to any one of (1) to (11) mentioned above, wherein the nanoparticle of an inorganic metal atom or an inorganic metal compound may be a metal nanoparticle; (13) the nanographite structure/metal nanoparticle composite according to any one of (1) to (11) mentioned above, wherein the nanoparticle of an inorganic metal atom or an inorganic metal compound may be a metal compound nanoparticle; (14) the nanographite structure/metal nanoparticle composite according to (13) mentioned above, wherein the metal compound nanoparticle may be a metal oxide nanoparticle; (15) the nanographite structure/metal nanoparticle composite according to (13) mentioned above, wherein the metal compound nanoparticle may be a magnetic material nanoparticle; (16) the nanographite structure/metal nanoparticle composite according to any one of (1) to (15) mentioned above, wherein the metal may be iron, beryllium, gallium, manganese, phosphorus, uranium, lead, cobalt, nickel, zinc, cadmium or chromium; (17) the nanographite structure/metal nanoparticle composite according to any one of (1) to (11) mentioned above, wherein the nanoparticle of an inorganic metal atom or an inorganic metal compound may be a nanoparticle of iron oxide, a nanoparticle of cadmium selenide, a nanoparticle of zinc selenide, a nanoparticle of zinc sulfide, or a nanoparticle of cadmium sulfide; (18) the nanographite structure/metal nanoparticle composite according to any one of (1) to (17) mentioned above, wherein the nanographite structure may be a carbon nanotube or a carbon nanohorn; (19) the nanographite structure/metal nanoparticle composite according to (18) mentioned above, wherein the carbon nanotube or the carbon nanohorn may be constituted of a carbon structure to which a functional group is added; (20) the nanographite structure/metal nanoparticle composite according to any one of (1) to (19) mentioned above, wherein the nanographite structure may be two-dimensionally aligned on a substrate; (21) the nanographite structure/metal nanoparticle composite according to any one of (1) to (19) mentioned above, wherein the metal nanoparticle may be two-dimensionally aligned on a substrate; and (22) the nanographite structure/metal nanoparticle composite according to (20) mentioned above, wherein the cage protein may be removed.

The present invention also relates to: (23) a protein wherein a nanographite structure recognition peptide may be fused or chemically bound to a surface of a cage protein; (24) the protein according to (23) mentioned above, wherein the cage protein may belong to a ferritin protein family; (25) the protein according to (24) mentioned above, wherein the ferritin protein family may be ferritin; (26) the protein according to (25) mentioned above, wherein the ferritin may be higher eukaryote-derived ferritin; (27) the protein according to (26) mentioned above, wherein the higher eukaryote-derived ferritin may be horse spleen-derived type L ferritin; (28) the protein according to (24) mentioned above, wherein the ferritin protein family may be derived from a bacterium; (29) the protein according to (23) mentioned above, wherein the cage protein may be a viral particle; (30) the protein according to any one of (23) to (29) mentioned above, wherein the nanographite structure recognition peptide may be a peptide consisting of an amino acid sequence shown by any one of SEQ ID NOs: 1 to 20; (31) the protein according to any one of (23) to (29) mentioned above, wherein the nanographite structure recognition peptide may be a peptide containing whole or part of an amino acid sequence shown by any one of SEQ ID NOs: 1 to 20 and may be capable of binding to a nanographite structure; (32) the protein according to (30) or (31) mentioned above, wherein the amino acid sequence shown by any one of SEQ ID NOs: 1 to 20 may be DYFSSPYYEQLF (SEQ ID NO: 1); (33) the protein according to (30) or (31) mentioned above, wherein the amino acid sequence shown by any one of SEQ ID NOs: 1 to 20 may be YDPFHII (SEQ ID NO: 2); (34) the protein according to any one of (23) to (33) mentioned above, wherein the nanoparticle of an inorganic metal atom or an inorganic metal compound may be a metal nanoparticle; (35) the protein according to any one of (23) to (33) mentioned above, wherein the nanoparticle of an inorganic metal atom or an inorganic metal compound may be a metal compound nanoparticle; (36) the protein according to (35) mentioned above, wherein the metal compound nanoparticle may be a metal oxide nanoparticle; (37) the protein according to (35) mentioned above, wherein the metal compound nanoparticle may be a magnetic material nanoparticle; (38) the protein according to any one of (22) to (36) mentioned above, wherein the metal may be iron, beryllium, gallium, manganese, phosphorus, uranium, lead, cobalt, nickel, zinc, cadmium or chromium; (39) the protein according to (23) mentioned above, wherein the nanoparticle of an inorganic metal atom or an inorganic metal compound may be a nanoparticle of iron oxide, a nanoparticle of cadmium selenide, a nanoparticle of zinc selenide, a nanoparticle of zinc sulfide, or a nanoparticle of cadmium sulfide; (40) the protein according to any one of (23) to (39) mentioned above, wherein the nanographite structure may be a carbon nanotube or a carbon nanohorn; and (41) the protein according to (40) mentioned above, wherein the carbon nanotube or the carbon nanohorn may be constituted of a carbon structure to which a functional group is added.

The present invention further relates to: (42) a method for retaining a nanoparticle of an inorganic metal atom or an inorganic metal compound in an interior space of the protein according to any one of (23) to (41) mentioned above, and supporting a plurality of nanoparticles of an inorganic metal atom or an inorganic metal compound on a nanographite structure with the use of affinity of the nanographite structure recognition peptide to the nanographite structure; (43) a method for producing a composite of a nanographite structure and nanoparticles of an inorganic metal compound, which may comprise the following steps: (i) retaining a nanoparticle of an inorganic metal atom or an inorganic metal compound in an interior space of the protein according to any one of (23) to (41) mentioned above; (ii) supporting a plurality of nanoparticles of an inorganic metal atom or an inorganic metal compound on a nanographite structure with the use of affinity of the nanographite structure recognition peptide to the nanographite structure; and (iii) removing a protein moiety by a heat treatment; (44) a method for producing a composite of a nanographite structure and nanoparticles of an inorganic metal compound, which may comprise the steps of: (i) retaining a nanoparticle of an inorganic metal atom or an inorganic metal compound in an interior space of the protein according to any one of (23) to (41) mentioned above; (ii) supporting a plurality of nanoparticles of an inorganic metal atom or an inorganic metal compound on a nanographite structure with the use of affinity of the nanographite structure recognition peptide to the nanographite structure; and (iii) removing a protein moiety by an electron beam treatment; (45) a method for aligning a nanographite structure by binding the nanographite structure to the protein according to any one of (23) to (41) mentioned above which has formed a two-dimensional crystal; and (46) a method for aligning a nanographite structure by binding the nanographite structure to the protein according to any one of (23) to (41) mentioned above which has formed a two-dimensional array.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawing, in which.

DETAILED DESCRIPTION

Figure 1:
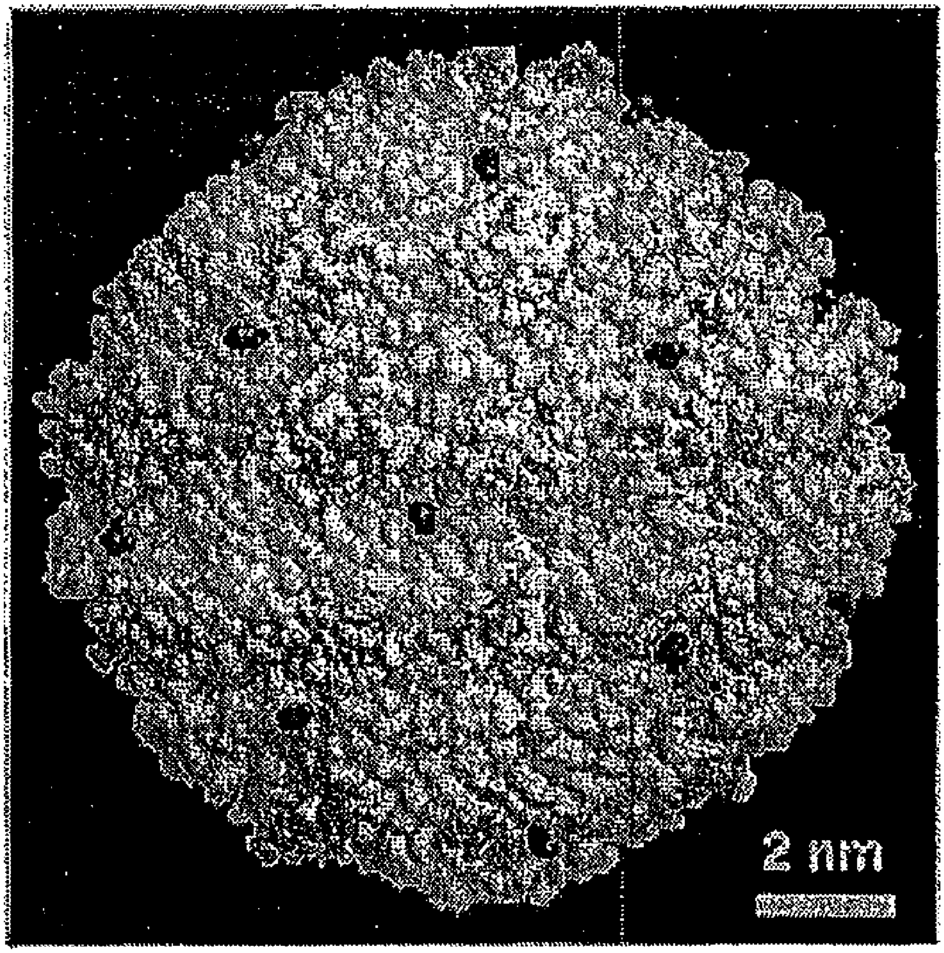
FIG. 1 illustrates the crystal structure of horse spleen-derived type L ferritin (LF) and the presentation site of DYFSSPYYEQLF (SEQ ID NO: 1; N1 sequence). N-terminal site of the crystal structure of horse spleen-derived type L ferritin (LF0) is indicated in red. Because the N-terminal of LF0 is located outside of the molecule, a multiple number of N1 sequence can be presented by fusing the N-terminal with N1 sequence.

The nanographite structure/metal nanoparticle composite of the present invention is not particularly limited as long as it is a composite wherein a nanoparticle of an inorganic metal atom or an inorganic metal compound is retained in an interior space of a protein in which a nanographite structure recognition peptide is fused or chemically bound to a surface of a cage protein, and wherein a plurality of nanoparticles of an inorganic metal atom or an inorganic metal compound are supported on a nanographite structure with the use of affinity of the nanographite structure recognition peptide to the nanographite structure. In addition, the protein is not particularly limited as long as it is a protein wherein a nanographite structure recognition peptide is fused or chemically bound to a surface of a cage protein. Here, the cage protein of the present invention means a protein having a space inside it and capable of containing a substance.

Examples of the above-mentioned cage protein include ferritin protein family, those derived from bacteria, and viral particles. As the ferritin protein family, ferritin and apoferritin are exemplified; for example, type L or type H ferritin derived from higher eukaryotes such as horse spleen-derived type L ferritin is preferably exemplified. Examples of the cage proteins derived from bacteria include DpsA protein and MrgA protein, and examples of the viral particles include viral particles of retrovirus, adenovirus, rotavirus, poliovirus, cytomegalovirus, cauliflower mosaic virus, etc.

Examples of the above-mentioned nanographite structure include carbon nanotubes and carbon nanohorns, and in addition, a modified nanographite structure wherein a carbon nanotube or a carbon nanohorn is constituted of a carbon structure to which a functional group such as an amino group, a hydroxyl group, and a carboxyl group is added.

As the above-mentioned nanographite structure recognition peptide, a peptide consisting of an amino acid sequence shown by any one of SEQ ID NOS: 1 to 20 (Japanese Laid-Open Patent Application No. 2004-121154; Langmuir, 20, 8939-8941, 2004), and a peptide containing whole or part of an amino acid sequence shown by any one of SEQ ID NOS: 1 to 20 and capable of binding to a nanographite structure, are exemplified. Among them, a peptide of DYFSSPYYEQLF (SEQ ID NO: 1) and a peptide of YDPFHII (SEQ ID NO: 2) are preferably exemplified.

The site on the cage protein surface to which a nanographite structure recognition peptide is fused or chemically bound is not particularly limited as long as it is a site where the nanographite structure recognition peptide can be bound to a nanographite structure. For example, in the case of ferritin, a loop structure site exposed on the ferritin surface, are exemplified in addition to amino terminals.

With regard to the method for fusing a nanographite structure recognition peptide to the surface of a cage protein such as ferritin, as described in Examples, the method can be conducted in accordance with the methods described in "Molecular Cloning: A Laboratory Manual, 2nd Ed., Cold Spring Harbor Laboratory, Cold Spring Harbor, N.Y., 1989", "Current Protocols in Molecular Biology, Supplement 1-38, John Wiley & Sons (1987-1997)", etc. Further, as the method for chemically binding a nanographite structure recognition peptide to the surface of a cage protein such as ferritin, the methods described in the literature (Proteins second edition, T. E. Creighton, W.H. Freeman and Company, New York, 1993; and G. T. Hermanson, in Bioconjugate Techniques, ed. G. T. Hermanson, Academic Press, San Diego Calif., 1996, pp. 169-186.) are exemplified.

Examples of the above-mentioned nanoparticles of an inorganic metal atom or an inorganic metal compound include: nanoparticles of metals such as iron, beryllium, gallium, manganese, phosphorus, uranium, lead, cobalt, nickel, zinc, cadmium or chromium; and nanoparticles of metal compounds such as nanoparticles of oxides, hydroxides, carbonate, etc. of these metals and nanoparticles of magnetic materials. Preferable examples include nanoparticles of iron oxide, nanoparticles of cadmium selenide, nanoparticles of zinc selenide, nanoparticles of zinc sulfide, and nanoparticles of cadmium sulfide.

By further fusing or chemically binding a functional peptide (e.g., a peptide capable of binding to titanium) to the above-mentioned protein wherein a nanographite structure recognition peptide is fused or chemically bound to a surface of a cage protein, it is also possible to align nanographite structures on a titanium substrate, and moreover, to support a plurality of nanoparticles on the nanographite structures.

In the case of cage proteins such as ferritin capable of forming two-dimensional crystals, nanometer-sized pattern making are made possible by two-dimensional crystallization of the cage proteins. For instance, a nanographite structure/metal nanoparticle composite wherein nanographite structures are two-dimensionally aligned on a substrate, and a nanographite structure/metal nanoparticle composite wherein metal nanoparticles are two-dimensionally aligned on a substrate can be obtained by the process comprising the following steps: (1) retaining a nanoparticle of an inorganic metal atom or an inorganic metal compound in an interior space of a protein wherein a nanographite structure recognition peptide is fused or chemically bound to a surface of a cage protein; (2) supporting a plurality of nanoparticles of an inorganic metal atom or an inorganic metal compound on a nanographite structure with the use of affinity of the nanographite structure recognition peptide to the nanographite structure; and (3) removing a protein moiety by a heat treatment or an electron beam treatment. The composite thus obtained can be the basic technique for high integration of memory devices, etc., in the field of semiconductors including memory devices.

In addition, a nanographite structure/metal nanoparticle composite wherein nanographite structures are two-dimensionally aligned on a substrate, and a nanographite structure/metal nanoparticle composite wherein metal nanoparticles are two-dimensionally aligned on a substrate can be obtained also by constituting cage proteins into a two-dimensional array. This can be achieved, for example, by the method for immobilizing proteins on a substrate by forming a cross-linking between proteins or proteins and the substrate with the use of reactivity between a compound having a plurality of functional groups such as glutaraldehyde and a side chain of an amino acid which constitutes the protein. Alternatively, this can be obtained by the method for immobilizing proteins by placing SAM (molecules capable of self-assembling into membranes) having a functional group on a substrate and forming a linkage between the functional group and a side chain of an amino acid which constitutes the protein. The composite thus obtained can be the basic technique for high integration of memory devices, etc., in the field of semiconductors including memory devices.

The invention will now be further described by way of the following non-limiting examples which further illustrate the invention, and are not intended, nor should they be interpreted to, limit the scope of the invention.

EXAMPLES

Example 1

The preparation of DNA (pKIS2) for expressing the fusion ferritin protein (N1-LF, FIG. 1), wherein a nanographite structure recognition peptide consisting of the amino acid sequence shown by SEQ ID NO: 1 (N1) is fused with horse spleen-derived type L ferritin (LF), was conducted in accordance with the following procedure.

In brief, an annealing reaction was conducted by mixing 100 pmole/μl each of synthetic DNAs of SEQ ID NOs: 22 and 23 in 50 mM NaCl, 10 mM Tris-HCl, 10 mM $MgCl_2$. The synthetic DNAs of SEQ ID NOs: 22 and 23 are complementary to each other and encode Met, an initiation codon, and subsequently the amino acid sequence shown by SEQ ID NO: 21, and have a restriction enzyme BamHI linker sequence on the initiation codon side, and a restriction enzyme SalI linker sequence on the opposite side. The resultant mixture was heated at 70° C. for 10 minutes and then slowly cooled to room temperature. Then, cDNA of horse spleen-derived type L ferritin digested a plasmid pKITO which had been cloned into downstream of tac promoter (Okuda et al. 2003, Biotechnology and Bioengineering, Vol 84, No. 2, p 187-194) with restriction enzymes BamHI and SalI. A large DNA fragment, about 6 kb, separated by 1% agarose gel electrophoresis was purified with Gene Clean II kit (BIO101). The purified substance was mixed with the aforementioned annealed DNA, and bound by using T4 DNA ligase.

Figure 2:
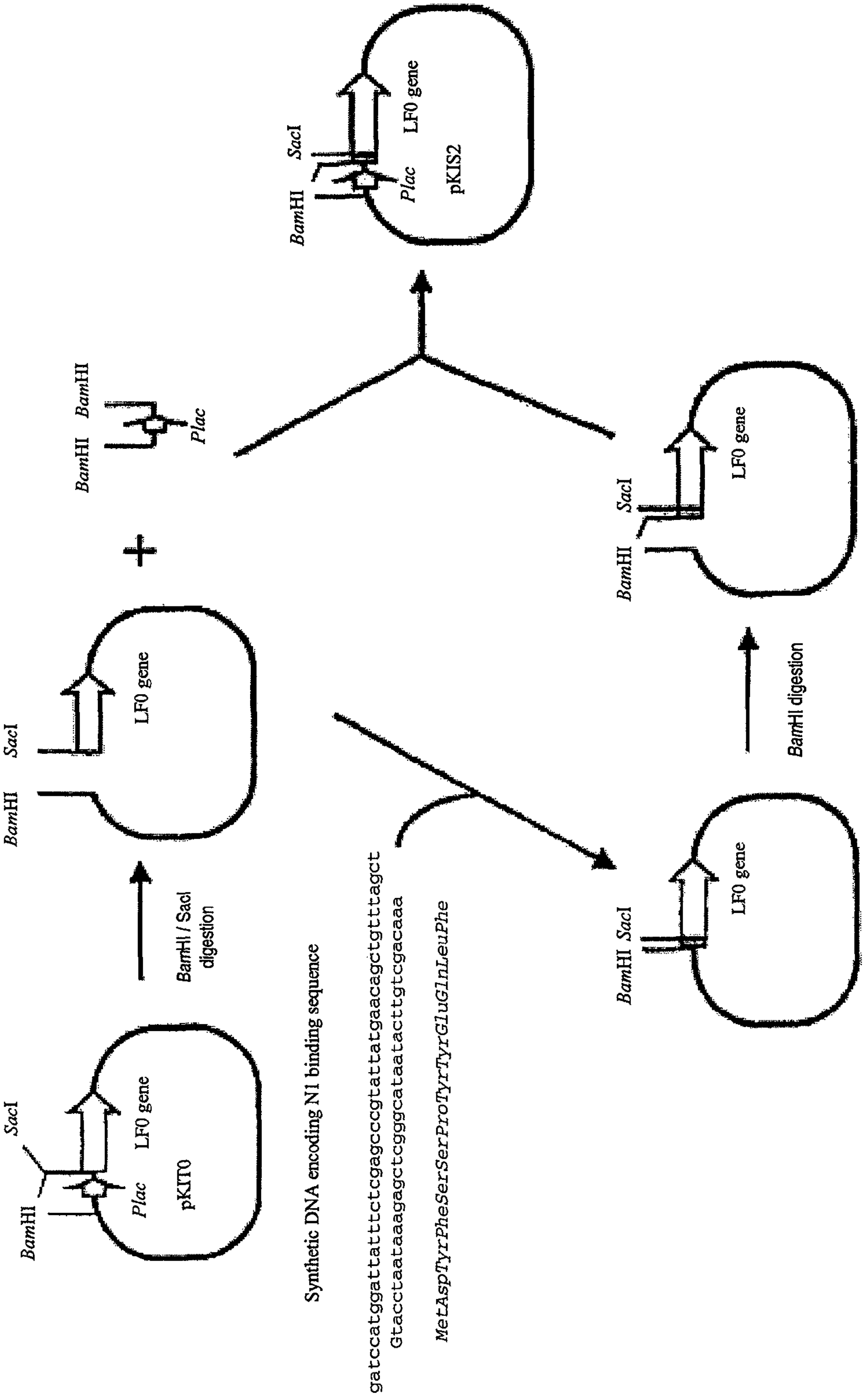
FIG. 2 illustrates a frame format of the construction of N1-LF expression vector pKIS2. N1-LF recombinant ferritin expression vector pKIS2 was constructed by the process comprising the steps of: (i) cutting pKITO, a horse spleen-derived type L ferritin expression vector, with restriction enzymes BamHI and SacI; (ii) inserting synthetic DNAs of SEQ ID NOs: 22 and 23 which had been annealed, and (iii) cutting the resultant product with BamHI; to that site, inserting a short DNA fragment produced when pKITO had been cut with BamHI.

Next, this DNA and pKITO were digested by BamHI respectively. The DNA fragments were separated by 1% agarose gel electrophoresis, wherein the former was a fragment of about 6 kb, and the latter was a fragment of about 300 bp. The DNA fragments were purified with Gene Clean II kit (BIO101), and the purified substances were bound by using T4 DNA ligase. The bound DNA was cloned into *E. coli* XLI-blue strain (hsdR17, supE44, recA1, endA1, gyrA46, thi, relA1, lac/F' [proAB+, $lacI^q\Delta$ (lacZ) M15; Tn10 (tetR)]) in accordance with an ordinary method (Molecular Cloning Third Edition, Cold Spring Harbor Laboratory Press), and a clone—into which a BamHI fragment of about 300 bp was inserted in the desired direction—was determined by a dideoxy termination method (CEQ DTCS Quick start kit, Beckman, Calif.), through DNA sequencing with the use of a primer (SEQ ID NO: 24) in a BamHI fragment of about 300 bp from pKITO. For the migration and data analysis of the reactant, an automated capillary sequencer (CEQ2000, Beckman) was used (FIG. 2).

The fusion ferritin protein wherein a nanographite structure recognition peptide is fused with horse spleen-derived type L ferritin was expressed and purified as follows. The *E. coli* XLI-blue strain was transformed with pKIS2 in accordance with an ordinary method, and a colony was picked up with a sterilized pick and shaking-cultured in 5 ml of LB medium at 37° C. for 16 to 18 hours. Then this culture solution was transplanted to 1 liter of LB medium and shaking-culture was conducted at 37° C. for another 16 to 18 hours. The *E. coli* was collected by centrifugation (Beckman J2-21M, JA-14 rotor, 5000 rpm, 5 minutes). The *E. coli* thus collected was washed with 80 ml of 50 mM Tris-HCl, pH 8.0, and collected by centrifugation (Kubota, 5922, RA410M2 rotor, 4000 rpm, 10 minutes) again. The collected *E. coli* was suspended in 30 ml of 50 mM Tris-HCl, pH 8.0, and an ultrasonic disruptor (BRANSON, SONIFIER 250, micro tip, output level maximum, duty cycle 50%, 2 minutes; this procedure was repeated 3 to 4 times) was used to obtain a solution of disrupted *E. coli* cells. The solution of disrupted *E. coli* cells was subjected to centrifugation (Kubota, 5922, RA410M2 rotor, 8000 rpm, 30 minutes) to collect soluble fractions. By putting the fractions into a warm bath at 65° C. for 20 minutes, coexisting proteins were denatured. The denatured coexisting proteins which formed precipitates were removed by centrifugation (Kubota, 5922, RA410M2 rotor, 8000 rpm, 30 minutes), and the supernatant was collected.

Then, 5 M NaCl was added to the collected supernatant, such that the final concentration was adjusted to 0.5 M, and the resultant mixture was stirred and allowed to stand still at room temperature for 5 to 10 minutes, followed by collection of a precipitate by centrifugation (Kubota, 5922, RA410M2 rotor, 5000 rpm, 10 minutes). The precipitate was dissolved in 20 ml of 50 mM Tris-HCl (pH 8.0). Thereafter, 5 M NaCl was added again to this mixture such that the final concentration was adjusted to 0.5 M, and the resultant mixture was stirred and allowed to stand still at room temperature for 5 to 10 minutes; then a precipitate was collected by centrifugation (Kubota, 5922, RA410M2 rotor, 5000 rpm, 10 minutes). The precipitate was further dissolved in 20 ml of 50 mM Tris-HCl (pH 8.0), and 5 M NaCl was added again to this mixture such that the final concentration was adjusted to 0.375 M this time. The resultant mixture was stirred and allowed to stand still at room temperature for 5 to 10 minutes, and then a precipitate was collected by centrifugation (Kubota, 5922, RA410M2 rotor, 5000 rpm, 10 minutes). The collected precipitate was dissolved in 10 ml of 50 mM Tris-HCl (pH 8.0).

Figure 3:
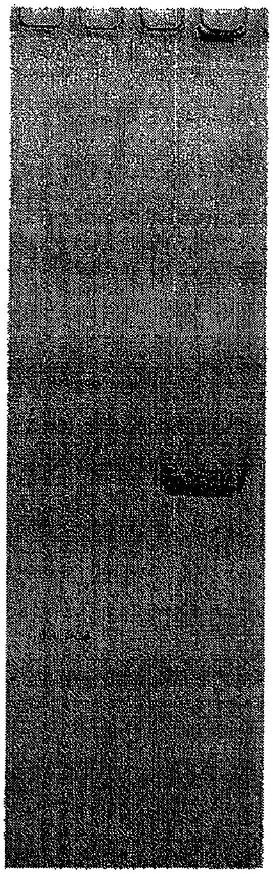
FIG. 3 shows the result of polyacrylamide gel electrophoresis of the final purified preparation of N1-LF. By polyacrylamide gel electrophoresis of 3 μg of the final purified preparation of N1-LF, the uniformity was evaluated. When the preparation was separated by using a concentration gradient gel (15 to 25%) and stained with Coomassie brilliant blue, a protein band was observed only at the position corresponding to the molecular weight of the desired N1-LF. Based on the observation, it was possible to confirm the preparation was highly pure. The left lane indicates molecular weight markers corresponding to 97.4, 66.3, 42.4, 30.0, 20.1, 14.4 kDa in descending order. The right lane indicates the final purified preparation of N1-LF.

In addition, the purification by gel filtration chromatography was conducted as needed. In other words, 200 to 500 μl of the purified preparation mentioned above was poured into an SW4000XL column (TOSOH) equilibrated with 50 mM Tris-HCl (pH 7.5), 150 mM NaCl, and 1 mM NaN3. Purification and separation were conducted by chromatography at a flow rate of 1 ml/min, and a fraction corresponding to a ferritin 24-mer was collected (FIG. 3).

Example 2

It was confirmed by the following procedure that as in the case of recombinant apoferritin, the N1-LF obtained in Example 1 has an ability to form nanoparticles of iron oxide in its interior space.

Figure 4:
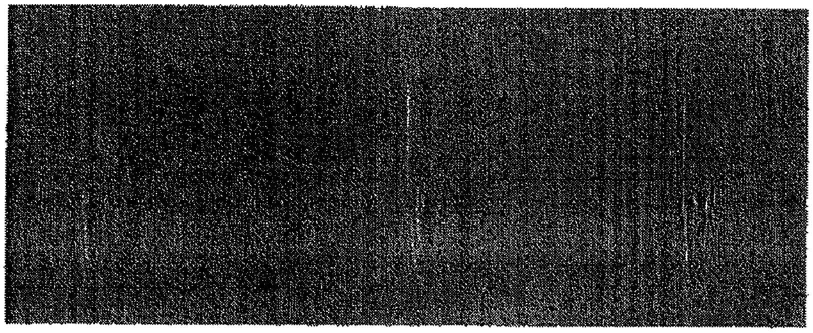
FIG. 4 shows the formation of nanoparticles of iron oxide in the interior space of N1-LF. This is an appearance of the solution at the time when nanoparticles of iron oxide were formed in the interior space of N1-LF. In control, no ferritin protein solution was contained. It can be seen from the color of the solution that nanoparticles of iron oxide were formed in the interior space of ferritin.
Figure 5:
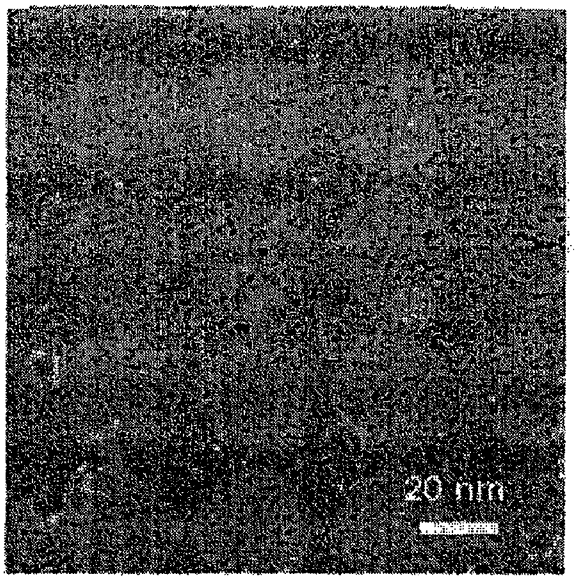
FIG. 5 is a photomicrograph taken by a transmission electron microscope showing the formation of nanoparticles of iron oxide in the interior space of N1-LF. The image of N1-LF stained with 1% aurothioglucose was observed with a JEOL1010, manufactured by JEOL Ltd., at 100 kV.

Firstly, 50 mM ammonium iron (II) sulfate hexahydrate was added to a solution comprising 50 mM HEPES-NaOH (pH 7.0) and 0.5 mg/ml N1-LF at an amount 1/10 of the volume of the solution (final concentration 5 mM), and the resultant mixture was allowed to stand still at room temperature overnight (FIG. 4). Subsequently, a procedure to precipitate excessive iron oxides by centrifugation (Kubota, 5922, RA410M2 rotor, 3000 rpm, 10 minutes) and remove them was repeated twice. Next, N1-LF was precipitated by a centrifugal operation with the use of an ultracentrifuge (Beckman, TLA 100.4 rotor, 50,000 rpm, 1 hour). This precipitate was dissolved in 50 mM Tris-HCl (pH 8.0), overlaid on an equal amount of 15% sucrose solution, and N1-LF present in sucrose fractions was collected by conducting a centrifugal operation again with the use of the ultracentrifuge (Beckman, TLA 100.4 rotor, 50,000 rpm, 1 hour). With regard to the collected N1-LF, the formation of nanoparticles of iron oxide was confirmed by a transmission electron microscope (JEOL1010, 100 kV, stained with 1% aurothioglucose, FIG. 5). The collected N1-LF was dialyzed against 50 mM Tris-HCl (pH 8.0), and then quantitated by BioRad Protein Assay (BioRad) and used for other experiments.

Example 3

Comparative Example 1

With regard to the horse spleen-derived type L ferritin (LF0), a recombinant was used as in the case of Example 1. The recombinant was prepared as follows. The *E. coli* XLI-blue strain was transformed with pKITO in accordance with an ordinary method, and a colony was picked up with a sterilized pick and shaking-cultured in 5 ml of LB medium at 37° C. for 16 to 18 hours. Then this culture solution was transplanted to 1 liter of LB medium and shaking-culture was conducted at 37° C. for another 16 to 18 hours. The *E. coli* was collected by centrifugation (Beckman J2-21M, JA-14 rotor, 5000 rpm, 5 minutes). The *E. coli* thus collected was washed with 80 ml of 50 mM Tris-HCl (pH 8.0), and collected by centrifugation (Kubota, 5922, RA410M2 rotor, 4000 rpm, 10 minutes) again. The collected *E. coli* was suspended in 30 ml of 50 mM Tris-HCl (pH 8.0), and then an ultrasonic disruptor (BRANSON, SONIFIER 250, micro tip, output level maximum, duty cycle 50%, 2 minutes; this procedure was repeated 3 to 4 times) was used to obtain a solution of disrupted *E. coli* cells. The solution of disrupted *E. coli* cells was subjected to centrifugation (Kubota, 5922, RA410M2 rotor, 8000 rpm, 30 minutes) to collect soluble fractions. By putting the fractions into a warm bath at 65° C. for 20 minutes, coexisting proteins were denatured. The denatured coexisting proteins which formed precipitates were removed by centrifugation (Kubota, 5922, RA410M2 rotor, 8000 rpm, 30 minutes), and the supernatant was collected.

The supernatant was poured into Q-sepharose HP (Amersham), which is a carrier for anion exchange chromatography, equilibrated with 50 mM Tris-HCl (pH 8.0), and the elution was conducted with 100 ml of 100 to 500 mM sodium chloride concentration gradient (3 ml/min). About 40 ml of fractions containing LF0 was concentrated by Centriprep 10 (Amicon) to 2.5 to 3 ml, and the resultant was poured into a 60 cm-long gel filtration chromatograph Sephacryl S-400 equilibrated with 50 mM Tris-HCl (pH 8.0), and 150 mM NaCl (herein after referred to as TBS); chromatography was conducted at a flow rate of 1.5 ml/min. Up to 100 μl of each fraction containing LF0 was poured into an SW4000XL column equilibrated with 50 mM Tris-HCl pH 7.5, 150 mM NaCl, and 1 mM NaN3, and analyzed by chromatography at a flow rate of 1 ml/min. A fraction corresponding to a ferritin 24-mer was confirmed and used for the experiment described below.

Example 4

Comparative Example 2

Figure 6:
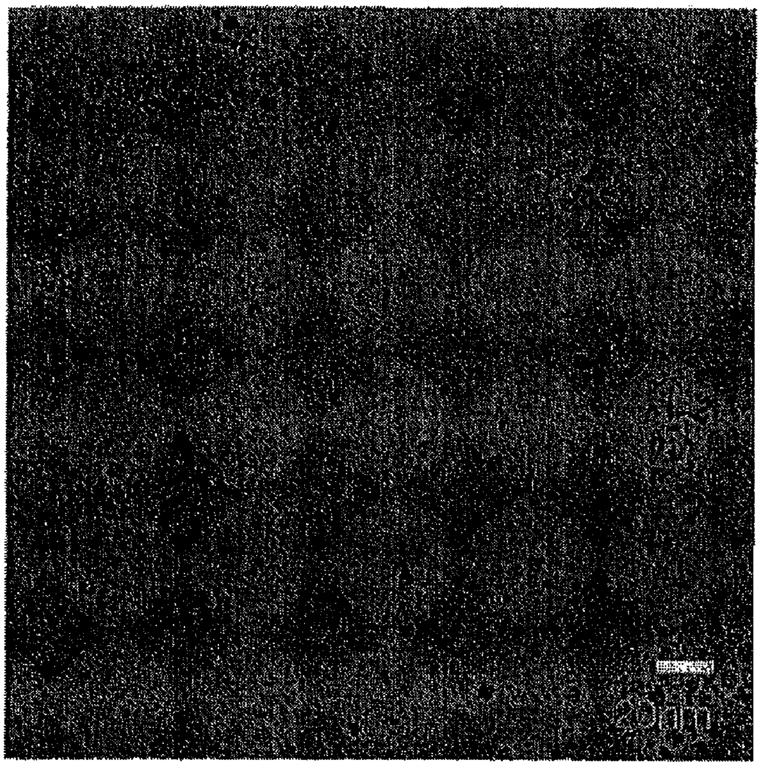
FIG. 6 is a photomicrograph taken by a transmission electron microscope showing the formation of nanoparticles of iron oxide in the interior space of LF0. The image of N1-LF stained with 1% aurothioglucose was observed with a JEOL1010, manufactured by JEOL Ltd., at 100 kV.

The formation of nanoparticles of iron oxide in the interior space of LF0 obtained in Example 3 was conducted in a same procedure as described in Example 2. The formation of nanoparticles was confirmed in a same manner as described in Example 2, as well (FIG. 6).

Example 5

The following experiment was conducted in order to show that though the N1-LF (SEQ ID NO: 26) having nanoparticles of iron oxide in its interior space obtained in Example 2 specifically binds to a nanographite structure, the LF0 (SEQ ID NO: 25) having nanoparticles of iron oxide in its interior space obtained in Example 4 cannot bind to a nanographite structure.

High-power $CO_2$ gas laser beam (output power 100 W, pulse width 20 ms, continuous wave) was emitted over the surface of carbon in a form of a sintered round bar in ambient pressure of 6×104 Pa of Ar gas, and the resultant soot-like substance was suspended in ethanol. Then ultrasonic agitation (frequency 40 kHz, 60 minutes) and decantation were repeated 4 times to obtain single-wall carbon nanohorns. About 200 mg of the single-wall carbon nanohorns was put into 40 ml of nitric acid at a concentration of about 70%, and reflux was conducted for 1 hour at 130° C. After the reflux, the resultant was neutralized and washed by repeating dilution with ion-exchange water, centrifugation, and disposal of the supernatant. Water-soluble single-wall carbon nanohorns having a functional group (including a carboxyl group) were prepared.

Figure 7:
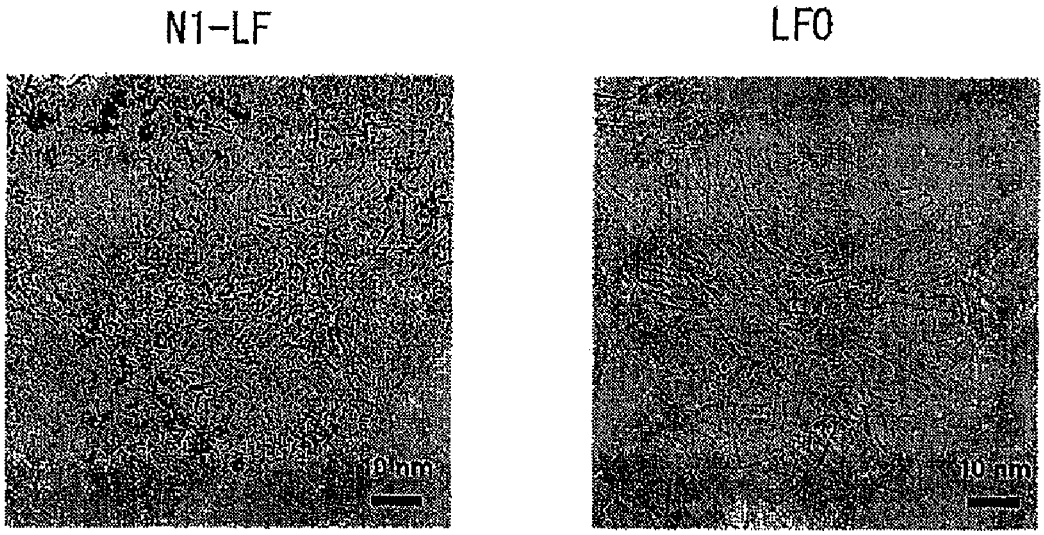
FIG. 7 shows nanoparticles of metal oxide supported on a carbon nanohorn. By presenting a peptide capable of binding to carbon nanohorns to ferritin protein, N1-LF could specifically support a plurality of nanoparticles of metal oxide on the carbon nanohorn as shown in the left image. With horse spleen-derived type L ferritin (LF0), it was impossible to support nanoparticles of metal oxide on the carbon nanohorn, as shown in the right image.

The carbon nanohorns were dissolved in 0.1% fetal bovine serum albumin, 0.05% polyoxyethylenesorbitan monolaurate (hereinafter referred to as "Tween 20" (Sigma, St. Louis)) contained in TBS (hereinafter referred to as "TBS-BT") such that the concentration was adjusted to 1 mg/ml. The carbon nanohorns were precipitated by a centrifugal operation (Kubota, 5922, AT-2018M rotor, 15000 rpm, 15 minutes), and the precipitate was suspended in TBS-BT such that the concentration was adjusted to 1 mg/ml. This operation was repeated 3 times, and subsequently the precipitated carbon nanohorns were suspended in TBS-BT containing N1-LF or LF0 having 0.1 mg/ml of nanoparticles of iron oxide in its core, such that the concentration was adjusted to 1 mg/ml. The suspension was rotated and stirred for 12 hours at room temperature with a rotator RT-50 manufactured by Taitec. In order to remove ferritin molecules which had not bound, the carbon nanohorns were precipitated by a centrifugal operation (Kubota, 5922, AT-2018M rotor, 15000 rpm, 15 minutes), and the precipitate was washed 5 times with 400 μl of TBS containing 0.05% Tween 20. Then the solution was substituted with sterilized water for the demineralization of the precipitate. Thus treated precipitate was observed under a transmission electron microscope (TOPCON EM-002B, accelerating voltage 120 kV), which revealed that a plurality of nanoparticles of iron oxide were supported on a carbon nanohorn when N1-LF was mixed with carbon nanohorns. On the other hand, regarding LF0, nanoparticles of iron oxide were not observed on carbon nanohorns. Based on these observations, it was confirmed that N1-LF has an ability to specifically bind to carbon nanohorns, and that the method for supporting nanoparticles on nanographite structures utilizing this ability is effective (FIG. 7).

Example 6

Hipco (Carbon Nanotechnologies Inc., Texas), a single-wall carbon nanotube synthesized by chemical vapor deposition, was treated with $1\times10^{-5}$ Torr for 5 hours at 1750° C.

Reflux was then conducted for 30 minutes at about 130° C. in nitric acid at a concentration of about 70%. After that, neutralization with sodium hydroxide and washing with distilled water were conducted, and single-wall carbon nanotubes having a functional group (including a carboxyl group) were prepared.

Figure 8:
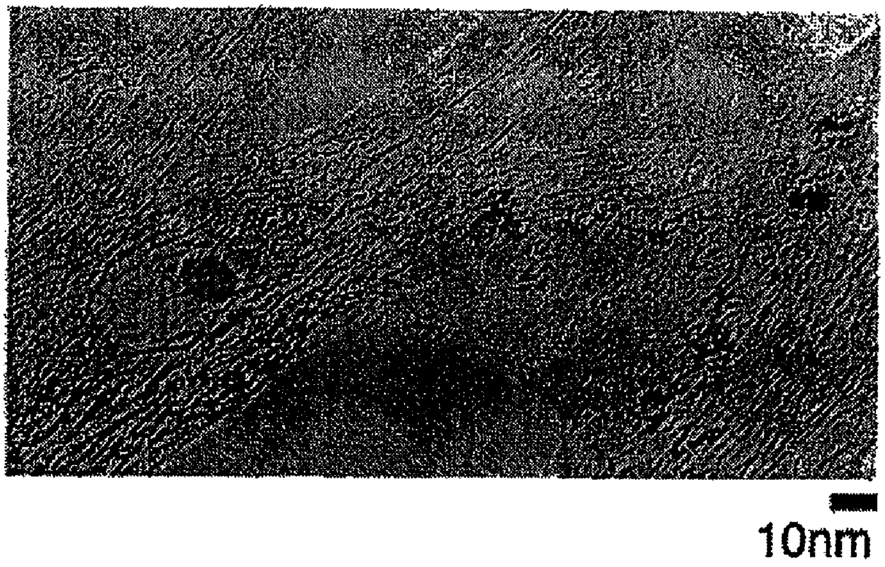
FIG. 8 shows nanoparticles of metal oxide supported on a single-wall carbon nanotube. By presenting a peptide capable of binding to carbon nanohorns to ferritin protein, N1-LF could support a plurality of nanoparticles of metal oxide on the single-wall carbon nanotube.

The single-wall carbon nanotubes were dissolved in TBS-BT in a same manner as described in Example 5. The single-wall carbon nanotubes were precipitated by a centrifugal operation (Kubota, 5922, AT-2018M rotor, 15000 rpm, 15 minutes), and the resultant precipitate was suspended in TBS-BT again. This operation was repeated 3 times, and subsequently the precipitated single-wall carbon nanotubes were suspended, in a same manner as described in Example 5, in TBS-BT containing N1-LF having nanoparticles of iron oxide in its core. The suspension was rotated and stirred for 12 hours at room temperature with a rotator RT-50 manufactured by Taitec. In order to remove ferritin molecules which had not bound, the single-wall carbon nanotubes were precipitated by a centrifugal operation (Kubota, 5922, AT-2018M rotor, 15000 rpm, 15 minutes), and the precipitate was washed 5 times with TBS containing 0.05% Tween 20. The solution was then substituted with sterilized water for the demineralization of the precipitate. Thus treated precipitate was observed under a transmission electron microscope (TOPCON EM-002B, 120 kV), and it was confirmed that a plurality of nanoparticles of iron oxide was supported on a carbon nanohorn when N1-LF was mixed with single-wall carbon nanotubes (FIG. 8).

INDUSTRIAL APPLICABILITY

The nanographite structure/metal nanoparticle composite of the present invention has clear industrial applications. For example, due to its mechanical and/or electrical properties, the composite can be used in structures ranging from clothes and sports gear to combat jackets and space elevators, as well as in semiconductors, fluorescent indicator tubes, fuel cells, and gas storage. Furthermore, the composite can also have biomedical/biotechnological applications, such as for vectors for gene therapy, cosmetics, drug delivery systems, and biosensors.

The invention is further described by the following numbered paragraphs:

1. A nanographite structure/metal nanoparticle composite, wherein a nanoparticle of an inorganic metal atom or an inorganic metal compound is retained in an interior space of a protein in which a nanographite structure recognition peptide is fused or chemically bound to a surface of a cage protein, and wherein a plurality of nanoparticles of an inorganic metal atom or an inorganic metal compound are supported on a nanographite structure with the use of affinity of the nanographite structure recognition peptide to the nanographite structure.

2. The nanographite structure/metal nanoparticle composite according to paragraph 1, wherein the cage protein belongs to a ferritin protein family.

3. The nanographite structure/metal nanoparticle composite according to paragraph 2, wherein the ferritin protein family is ferritin.

4. The nanographite structure/metal nanoparticle composite according to paragraph 3, wherein the ferritin is higher eukaryote-derived ferritin.

5. The nanographite structure/metal nanoparticle composite according to paragraph 4, wherein the higher eukaryote-derived ferritin is horse spleen-derived type L ferritin.

6. The nanographite structure/metal nanoparticle composite according to paragraph 1, wherein the cage protein is derived from a bacterium.

7. The nanographite structure/metal nanoparticle composite according to paragraph 1, wherein the cage protein is a viral particle.

8. The nanographite structure/metal nanoparticle composite according to any one of paragraphs 1 to 7, wherein the nanographite structure recognition peptide is a peptide consisting of an amino acid sequence shown by any one of SEQ ID NOs: 1 to 20.

9. The nanographite structure/metal nanoparticle composite according to any one of paragraphs 1 to 7, wherein the nanographite structure recognition peptide is a peptide containing whole or part of an amino acid sequence shown by any one of SEQ ID NOs: 1 to 20 and capable of binding to a nanographite structure.

10. The nanographite structure/metal nanoparticle composite according to paragraph 8 or 9, wherein the amino acid sequence shown by any one of SEQ ID NOs: 1 to 20 is DYFSSPYYEQLF (SEQ ID NO: 1).

11. The nanographite structure/metal nanoparticle composite according to paragraph 8 or 9, wherein the amino acid sequence shown by any one of SEQ ID NOs: 1 to 20 is YDPFHII (SEQ ID NO: 2).

12. The nanographite structure/metal nanoparticle composite according to any one of paragraphs 1 to 11, wherein the nanoparticle of an inorganic metal atom or an inorganic metal compound is a metal nanoparticle.

13. The nanographite structure/metal nanoparticle composite according to any one of paragraphs 1 to 11, wherein the nanoparticle of an inorganic metal atom or an inorganic metal compound is a metal compound nanoparticle.

14. The nanographite structure/metal nanoparticle composite according to paragraph 13, wherein the metal compound nanoparticle is a metal oxide nanoparticle.

15. The nanographite structure/metal nanoparticle composite according to paragraph 13, wherein the metal compound nanoparticle is a magnetic material nanoparticle.

16. The nanographite structure/metal nanoparticle composite according to any one of paragraphs 1 to 15, wherein the metal is iron, beryllium, gallium, manganese, phosphorus, uranium, lead, cobalt, nickel, zinc, cadmium or chromium.

17. The nanographite structure/metal nanoparticle composite according to any one of paragraphs 1 to 11, wherein the nanoparticle of an inorganic metal atom or an inorganic metal compound is a nanoparticle of iron oxide, a nanoparticle of cadmium selenide, a nanoparticle of zinc selenide, a nanoparticle of zinc sulfide, or a nanoparticle of cadmium sulfide.

18. The nanographite structure/metal nanoparticle composite according to any one of paragraphs 1 to 17, wherein the nanographite structure is a carbon nanotube or a carbon nanohorn.

19. The nanographite structure/metal nanoparticle composite according to paragraph 18, wherein the carbon nanotube or the carbon nanohorn is constituted of a carbon structure to which a functional group is added.

20. The nanographite structure/metal nanoparticle composite according to any one of paragraphs 1 to 19, wherein the nanographite structure is two-dimensionally aligned on a substrate.

21. The nanographite structure/metal nanoparticle composite according to any one of paragraphs 1 to 19, wherein the metal nanoparticle is two-dimensionally aligned on a substrate.

22. The nanographite structure/metal nanoparticle composite according to paragraph 20, wherein the cage protein is removed.

23. A protein wherein a nanographite structure recognition peptide is fused or chemically bound to a surface of a cage protein.

24. The protein according to paragraph 23, wherein the cage protein belongs to a ferritin protein family.

25. The protein according to paragraph 24, wherein the ferritin protein family is ferritin.

26. The protein according to paragraph 25, wherein the ferritin is higher eukaryote-derived ferritin.

27. The protein according to paragraph 26, wherein the higher eukaryote-derived ferritin is horse spleen-derived type L ferritin.

28. The protein according to paragraph 24, wherein the ferritin protein family is derived from a bacterium.

29. The protein according to paragraph 23, wherein the cage protein is a viral particle.

30. The protein according to any one of paragraphs 23 to 29, wherein the nanographite structure recognition peptide is a peptide consisting of an amino acid sequence shown by any one of SEQ ID NOs: 1 to 20.

31. The protein according to any one of paragraphs 23 to 29, wherein the nanographite structure recognition peptide is a peptide containing whole or part of an amino acid sequence shown by any one of SEQ ID NOs: 1 to 20 and capable of binding to a nanographite structure.

32. The protein according to paragraph 30 or 31, wherein the amino acid sequence shown by any one of SEQ ID NOs: 1 to 20 is DYFSSPYYEQLF (SEQ ID NO: 1).

33. The protein according to paragraph 30 or 31, wherein the amino acid sequence shown by any one of SEQ ID NOs: 1 to 20 is YDPFHII (SEQ ID NO: 2).

34. The protein according to any one of paragraphs 23 to 33, wherein the nanoparticle of an inorganic metal atom or an inorganic metal compound is a metal nanoparticle.

35. The protein according to any one of paragraphs 23 to 33, wherein the nanoparticle of an inorganic metal atom or an inorganic metal compound is a metal compound nanoparticle.

36. The protein according to paragraph 35, wherein the metal compound nanoparticle is a metal oxide nanoparticle.

37. The protein according to paragraph 35, wherein the metal compound nanoparticle is a magnetic material nanoparticle.

38. The protein according to any one of paragraphs 22 to 36, wherein the metal is iron, beryllium, gallium, manganese, phosphorus, uranium, lead, cobalt, nickel, zinc, cadmium or chromium.

39. The protein according to paragraph 23, wherein the nanoparticle of an inorganic metal atom or an inorganic metal compound is a nanoparticle of iron oxide, a nanoparticle of cadmium selenide, a nanoparticle of zinc selenide, a nanoparticle of zinc sulfide, or a nanoparticle of cadmium sulfide.

40. The protein according to any one of paragraphs 23 to 39, wherein the nanographite structure is a carbon nanotube or a carbon nanohorn.

41. The protein according to paragraph 40, wherein the carbon nanotube or the carbon nanohorn is constituted of a carbon structure to which a functional group is added.

42. A method for retaining a nanoparticle of an inorganic metal atom or an inorganic metal compound in an interior space of the protein according to any one of paragraphs 23 to 41, and supporting a plurality of nanoparticles of an inorganic metal atom or an inorganic metal compound on a nanographite structure with the use of affinity of the nanographite structure recognition peptide to the nanographite structure.

43. A method for producing a composite of a nanographite structure and nanoparticles of an inorganic metal compound, comprising the steps of: retaining a nanoparticle of an inorganic metal atom or an inorganic metal compound in an interior space of the protein according to any one of paragraphs 23 to 41; supporting a plurality of nanoparticles of an inorganic metal atom or an inorganic metal compound on a nanographite structure with the use of affinity of the nanographite structure recognition peptide to the nanographite structure; and removing a protein moiety by a heat treatment.

44. A method for producing a composite of a nanographite structure and nanoparticles of an inorganic metal compound, comprising the steps of: retaining a nanoparticle of an inorganic metal atom or an inorganic metal compound in an interior space of the protein according to any one of paragraphs 23 to 41; supporting a plurality of nanoparticles of an inorganic metal atom or an inorganic metal compound on a nanographite structure with the use of affinity of the nanographite structure recognition peptide to the nanographite structure; and removing a protein moiety by an electron beam treatment.

45. A method for aligning a nanographite structure by binding the nanographite structure to the protein according to any one of paragraphs 23 to 41 which has formed a two-dimensional crystal.

46. A method for aligning a nanographite structure by binding the nanographite structure to the protein according to any one of paragraphs 23 to 41 which has formed a two-dimensional array.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A nanographite structure/metal nanoparticle composite, comprising:

(a) a nanographite structure selected from carbon nanotube and carbon nanohorn;

(b) ferritin containing within its interior space a nanoparticle of an inorganic metal atom or an inorganic metal compound; and (c) a nanographite structure recognition peptide consisting of an amino acid sequence shown by DYFSSPYYEQLF (SEQ ID NO: 1) and that is fused to an N-terminal site of the ferritin;

wherein a plurality of the nanoparticles is supported on the nanographite structure through the affinity of the nanographite structure recognition peptide to the nanographite structure.

2. The nanographite structure/metal nanoparticle composite according to claim 1, wherein the ferritin is higher eukaryote-derived ferritin.

3. The nanographite structure/metal nanoparticle composite according to claim 2, wherein the higher eukaryote-derived ferritin is horse spleen-derived type L ferritin.

4. A nanographite structure/metal nanoparticle composite, comprising:

(a) a nanographite structure selected from carbon nanotube and carbon nanohorn;

(b) ferritin containing within its interior space a nanoparticle of an inorganic metal atom or an inorganic metal compound; and (c) a nanographite structure recognition peptide consisting of an amino acid sequence shown by YDPFHII (SEQ ID NO: 2) and that is fused to an N-terminal site of the ferritin;

wherein a plurality of the nanoparticles is supported on the nanographite structure through the affinity of the nanographite structure recognition peptide to the nanographite structure.

5. The nanographite structure/metal nanoparticle composite according to claim 1, wherein the nanoparticle is a metal nanoparticle.

6. The nanographite structure/metal nanoparticle composite according to claim 1, wherein the nanoparticle is a metal compound nanoparticle.

7. The nanographite structure/metal nanoparticle composite according to claim 6, wherein the metal compound nanoparticle is a metal oxide nanoparticle.

8. The nanographite structure/metal nanoparticle composite according to claim 6, wherein the metal compound nanoparticle is a magnetic material nanoparticle.

9. The nanographite structure/metal nanoparticle composite according to claim 1, wherein the metal is iron, beryllium, gallium, manganese, phosphorus, uranium, lead, cobalt, nickel, zinc, cadmium or chromium.

10. The nanographite structure/metal nanoparticle composite according to claim 1, wherein the nanoparticle is a nanoparticle of iron oxide, a nanoparticle of cadmium selenide, a nanoparticle of zinc selenide, a nanoparticle of zinc sulfide, or a nanoparticle of cadmium sulfide.

11. The nanographite structure/metal nanoparticle composite according to claim 1, wherein the carbon nanotube or the carbon nanohorn is constituted of a carbon structure to which a functional group is added.

12. The nanographite structure/metal nanoparticle composite according to claim 1, wherein the nanographite structure is two-dimensionally aligned on a substrate.

13. A method for adding and retaining a nanoparticle of an inorganic metal atom or an inorganic metal compound in an interior space of a ferritin in which a nanographite structure recognition peptide consisting of the amino acid sequence shown by DYFSSPYYEQLF (SEQ ID NO: 1) is fused to an N-terminal site of the ferritin; and supporting a plurality of the nanoparticles on a nanographite structure selected from carbon nanotube and a carbon nanohorn with the use of affinity of the nanographite structure recognition peptide to the nanographite structure.

14. A method for producing a composite of a nanographite structure selected from carbon nanotube and a carbon nanohorn, and nanoparticles of an inorganic metal compound, comprising the steps of:

(i) adding and retaining a nanoparticle of an inorganic metal atom or an inorganic metal compound in an interior space of a ferritin in which a nanographite structure recognition peptide consisting of the amino acid sequence shown by DYFSSPYYEQLF (SEQ ID NO: 1) is fused to an N-terminal site of the ferritin;

(ii) supporting a plurality of nanoparticles of an inorganic metal atom or an inorganic metal compound on the nanographite structure with the use of affinity of the nanographite structure recognition peptide to the nanographite structure; and (iii) removing the ferritin by a heat treatment.

15. A method for producing a composite of a nanographite structure selected from carbon nanotube and a carbon nanohorn and nanoparticles of an inorganic metal compound, comprising the steps of:

(i) adding and retaining a nanoparticle of an inorganic metal atom or an inorganic metal compound in an interior space of a ferritin in which a nanographite structure recognition peptide consisting of the amino acid sequence shown by DYFSSPYYEQLF (SEQ ID NO: 1) is fused to an N-terminal site of the ferritin;

(ii) supporting a plurality of nanoparticles of an inorganic metal atom or an inorganic metal compound on the nanographite structure with the use of affinity of the nanographite structure recognition peptide to the nanographite structure; and (iii) removing the ferritin by an electron beam treatment.

* * * * *